(12) United States Patent
Zhang et al.

(10) Patent No.: US 11,397,174 B2
(45) Date of Patent: Jul. 26, 2022

(54) SUSPENSION SLIDE RAIL PLATFORM-BASED GREENHOUSE INFORMATION AUTOMATIC MONITORING METHOD

(71) Applicant: JIANGSU UNIVERSITY, Jiangsu (CN)

(72) Inventors: Xiaodong Zhang, Jiangsu (CN); Pei Wang, Jiangsu (CN); Hanping Mao, Jiangsu (CN); Hongyan Gao, Jiangsu (CN); Zhiyu Zuo, Jiangsu (CN); Yixue Zhang, Jiangsu (CN)

(73) Assignee: JIANGSU UNIVERSITY

( * ) Notice: Subject to any disclaimer, the term of this patent is extended or adjusted under 35 U.S.C. 154(b) by 229 days.

(21) Appl. No.: 16/646,034

(22) PCT Filed: Nov. 16, 2018

(86) PCT No.: PCT/CN2018/115816
§ 371 (c)(1),
(2) Date: Mar. 10, 2020

(87) PCT Pub. No.: WO2019/134453
PCT Pub. Date: Jul. 11, 2019

(65) Prior Publication Data
US 2021/0364487 A1    Nov. 25, 2021

(30) Foreign Application Priority Data
Jan. 3, 2018    (CN) .......................... 201810004678.5

(51) Int. Cl.
*G06K 9/00*    (2022.01)
*G01N 33/00*    (2006.01)
(Continued)

(52) U.S. Cl.
CPC .......... *G01N 33/0098* (2013.01); *A01G 9/26* (2013.01); *G01J 1/4204* (2013.01); *G01J 5/00* (2013.01);
(Continued)

(58) Field of Classification Search
CPC ...... G01N 33/0098; A01G 9/26; A01G 9/143; G01J 1/4204; G01J 5/00; G01J 2005/0077;
(Continued)

(56) References Cited

U.S. PATENT DOCUMENTS

| 3,186,493 | A | * | 6/1965 | Barry | ..................... | A01B 79/00 |
| | | | | | | 172/26 |
| RE31,023 | E | * | 9/1982 | Hall, III | ................... | A01G 7/00 |
| | | | | | | 193/25 E |

(Continued)

FOREIGN PATENT DOCUMENTS

| CN | 102017938 | 4/2011 | .............. A01M 7/00 |
| CN | 102384767 | 3/2012 | .............. G01D 21/02 |

(Continued)

OTHER PUBLICATIONS

International Search Report and Written Opinion issued in PCT/CN18/115816, dated Jan. 30, 2019, with English translation, 14 pgs.

(Continued)

*Primary Examiner* — Shervin K Nakhjavan
(74) *Attorney, Agent, or Firm* — Hayes Soloway P.C.

(57) ABSTRACT

A greenhouse information automatic monitoring method, adopting a multi-sensor system, using binocular vision multi-function cameras combining with a laser ranging sensor and an infrared temperature measuring sensor, realizing online patrol monitoring of greenhouse crop comprehensive information of image and infrared temperature characteristics of plant nutrition, water, pest and disease (Continued)

damage as well as plant crown width, plant height, fruit and growth characteristics. The multi-sensor system is mounted on a suspension slide platform and combines with a lifting mechanism and an electric control rotation pan-tilt, such that not only accurate positioning and stationary point detection in the detection travelling direction can be realized, but also multi-sensor information patrol detection at different detection distances, different top view fields and different detection angles is realized.

6 Claims, 6 Drawing Sheets

(51) Int. Cl.
*A01G 9/26* (2006.01)
*G01J 1/42* (2006.01)
*G01J 5/00* (2022.01)
*G01S 17/08* (2006.01)
*G05B 19/042* (2006.01)
*G06T 7/00* (2017.01)

(52) U.S. Cl.
CPC .......... *G01S 17/08* (2013.01); *G05B 19/0428* (2013.01); *G06T 7/0016* (2013.01); *G01J 2005/0077* (2013.01); *G05B 2219/24015* (2013.01); *G06T 2207/10016* (2013.01); *G06T 2207/10048* (2013.01); *G06T 2207/30188* (2013.01)

(58) Field of Classification Search
CPC ........ G01S 17/08; G01S 7/4817; G01S 17/86; G01S 17/894; G05B 19/0428; G05B 2219/24015; G05B 23/02; G06T 7/0016; G06T 2207/10016; G06T 2207/10048; G06T 2207/30188; G06T 2207/10024; G06T 2207/10028; G06T 7/0012; Y02A 40/25; G01D 21/02
See application file for complete search history.

(56) References Cited

U.S. PATENT DOCUMENTS

| | | | |
|---|---|---|---|
| 4,612,996 A * | 9/1986 | Wolf | A01B 69/007 104/165 |
| 10,172,304 B2 * | 1/2019 | Ayers | C05D 9/02 |
| 10,597,896 B1 * | 3/2020 | Hamilton | E04H 15/10 |
| 11,287,411 B2 * | 3/2022 | Miresmailli | A01G 25/16 |
| 2015/0015697 A1 | 1/2015 | Redden | |

FOREIGN PATENT DOCUMENTS

| | | | |
|---|---|---|---|
| CN | 102721651 | 10/2012 | ............. G01N 21/25 |
| CN | 202773632 | 3/2013 | ............. A01G 31/02 |
| CN | 103264730 | 8/2013 | ............. B62D 55/06 |
| CN | 103488173 | 1/2014 | ............... G05D 1/02 |
| CN | 103699095 | 4/2014 | ........... G05B 19/418 |
| CN | 105825177 | 8/2016 | ............... G06K 9/00 |
| CN | 106323182 | 1/2017 | ............. G01B 11/08 |
| CN | 106406178 | 2/2017 | ........... G05B 19/042 |
| CN | 106441442 | 2/2017 | ............. G01D 21/02 |
| CN | 107486834 | 12/2017 | ................ B25J 5/02 |
| CN | 108362326 | 8/2018 | ............. G01D 21/02 |
| CN | 108387262 | 8/2018 | ............. G01D 21/02 |
| EP | 0 084 289 | 6/1986 | ............... A01G 9/24 |

OTHER PUBLICATIONS

U.S. Appl. No. 16/645,891, filed Mar. 10, 2020, Zhang et al.
International Search Report and Written Opinion issued in PCT/CN18/115817, dated Jan. 31, 2019, with English translation, 10 pgs.
Wang, et al., An Efficient and Labor Saving Pesticide Application Device and Method for Greenhouse, Greenhouse intelligent equipment series 33, Beijing Agricultural Intelligent Equipment Technology Research Center, Greenhouse & Horticulture, pp. 26-27, 2011. (with Machine translation).

* cited by examiner

SUSPENSION SLIDE RAIL PLATFORM-BASED GREENHOUSE INFORMATION AUTOMATIC MONITORING METHOD

I. TECHNICAL FIELD

The present invention belongs to the field of intelligent agricultural machinery, the utility model relates to an automatic monitoring method for comprehensive information of facilities environment and crops, especially a greenhouse information automatic monitoring method based on a suspended slide platform.

II. BACKGROUND ART

Presently, Chinese greenhouse planting area and yield are at the forefront in the world. However, most of the greenhouses in China still adopt the traditional planting irrigation model with large amount of water and fertilizer, which can't meet the demand of the cops owing to its blindness, and results in problems, such as low yield and quality of the crops, serious waste of resources, poor economic benefits. One of the main reasons is the lack of scientific management of the facilities and production; besides, it is difficult to obtain comprehensive information on the greenhouse crops and environment online and in real time to realize optimized regulation and control of water, fertilizer and environment on the basis of the actual demand of the crops and realize early warning against pests and diseases. In the past, manual and chemical methods are usually used for identification and detection of crop nutrition, growth and pests and diseases, which not only have low detection efficiency but also involve misjudgements, and might cause irreversible damages to crops. Owing to the unstructured environment of greenhouse planting and production, there are few advanced and applicable automatic monitoring equipment and methods for comprehensive information on greenhouse environment and crops that meet the actual production demands at present. The present invention employs a suspended rail-type detection platform to monitor plant growth and environment information automatically. The detection platform operates in an autonomous cruising mode and utilizes a multi-sensor detection system to collect comprehensive information on crop nutrition, growth, pests and diseases, and environment in a greenhouse. Compared with traditional methods and distributed detection methods, the method provided in the present invention greatly improves the accuracy of detection and identification, reduces the cost, and improves the operating efficiency.

The invention patent application No. CN201010519848.7 has disclosed a suspended self-propelled target spraying system, which comprises a guide rail, a self-propelled mobile platform, a Hall sensor, a spraying mechanical arm device, a binocular vision system, and a PLC logic controller, etc., wherein the guide rail is mounted on the greenhouse ceiling and the spraying mechanical arm is mounted on the self-propelled mobile platform. Therefore, pesticides can be sprayed automatically in the greenhouse environment to avoid physical injuries to the operators during the pesticide spraying process and the efficiency is improved. However, the device lacks a greenhouse environment information detection function, and doesn't take consideration of the environmental factors of the greenhouse adequately.

Ma Wei, et al. of Beijing Agricultural Intelligent Equipment Research Institute have developed a rail-type labor-saving operating apparatus for greenhouse. By connecting an installation rail to the structure of a greenhouse, the apparatus can be pushed by hand to travel smoothly with a mobile device, and all pesticide application and pressure boosting devices can be carried by the suspended platform. The apparatus solves the problems of large-area pesticide application to the greenhouse crops and inconvenience in transportation, and alleviates the labor intensity. However, it still requires certain manual operation, and its automation level is not high enough.

The invention patent application No. CN201310192634.7 has disclosed a tracked robot mobile platform, wherein a control module controls driving wheel train and driven wheel train to drive the car body to travel according to data signals from a monitoring module. As the tracks, wheel trains, and car body of the tracked robot all adopt rigid connections, the bumps on an uneven road, which may cause damages to the detecting equipment mounted on the mobile platform and affect the stability of detection, cannot be filtered out.

The invention patent application No. CN201010519848.7 has disclosed a suspended self-propelled targeting spraying system, comprising guide rail, self-propelled mobile platform, HS (Hall sensor), spraying mechanical arm device, binocular visual system, PLC logic controller etc. Because the invention is equipped with the guide rail on the ceiling of the greenhouse, and the spraying mechanical arm device is installed on the self-propelled mobile platform, it is capable of spraying pesticides automatically in the greenhouse environment, avoiding physical harm to the working staff during the process of pesticide-spraying and improving the efficiency. But the device of this invention is lack of detection of the environment information of the greenhouse, and the environmental factors of the greenhouse are not adequately considered in this invention. The invention patent application No. CN201310408112.6 has disclosed a multi-terrain intelligent mobile platform for detection, which comprises an autonomously travelling four-wheel carriage system and a four-axis rotor flight system, wherein the two systems are connected via a locking system and communicate with a PC terminal through a ZigBee wireless transmission network. The autonomously travelling four-wheel carriage system utilizes Arduino to control vehicle-mounted multi-parameter sensor module and driving module, etc.; the four-axis rotor flight system utilizes Arduino to control airborne multi-parameter sensor module and high-speed driving module, etc. When the platform encounters an insurmountable obstacle, the locking system can unlock automatically and thereby trigger the operation of the four-axis rotor flight system. The overall stability of the multi-terrain hybrid intelligent mobile platform is inferior to that of a mobile platform with an independent suspension system, whether it operates in a four-wheel mode or a flight mode. To operate in the flight mode, the mass of the airborne detecting equipment must be evenly distributed, and there is a limit to the weight of the airborne detecting equipment. Compared with single-mode mobile platforms, the multi-terrain hybrid intelligent mobile platform has a complex structure and a higher price.

In summary, as the existing intelligent mobile platforms are oriented to different task objectives, these platforms and the corresponding methods can't meet the requirements of greenhouse plant growth and environment information detection equipment for the detection accuracy and stability of a platform in unstructured greenhouse environments. It is difficult to realize automatic cruise detection of nutrition, growth, pest and disease information of crops in different growing stages, of different types, and in different plant sizes (small, medium and large) with existing intelligent mobile platforms and methods.

I. Contents of the Invention

The object of the present invention is to provide an automatic monitoring method for greenhouse information based on a suspended slide rail platform, so as to realize synchronous automatic cruise monitoring of crop nutrition, water, growth and pest and disease information in the greenhouse, as well as environmental lighting, temperature and humidity information in the greenhouse.

To attain the object described above, the present invention employs the following technical scheme:

1. An automatic monitoring method for greenhouse crop information based on a suspended slide rail platform, comprising the following steps:

S1: System Initialization:

Press the power button in a control cabinet to start up a monitoring system for comprehensive greenhouse information based on a suspended slide rail platform and let the system perform self-check, start up an industrial PC and switch on a touch display screen, start up a DSP movement controller and let a sliding platform return to zero position;

S2: System Setting:

2.1) Sample setting and sampling interval setting: set a plant spacing of the plants to be measured, and set landmarks, a movement interval of the sliding platform, and a sampling interval of a multi-sensor system;

2.2) Detection parameter setting: set detection modes and detection parameters, wherein the detection modes include four modes: crop nutrition stress detection, pest and disease detection, water stress detection and growth detection; wherein the parameter setting includes: nitrogen, phosphorus and potassium detection in the nutrition stress mode, species identification in the pest and disease detection mode, and plant height, crown width and fruits in the growth detection mode;

2.3) Sliding platform movement setting: set movement route and detection height of the sliding platform according to the detection parameters, crop growth period and species;

S3: Crop Information Detection:

3.1) Target Positioning of the Sliding Platform

According to the sampling interval set in 2.1), first, the DSP movement controller sends a signal to a deceleration motor according to a position instruction sent from the industrial PC, the deceleration motor drives a gear shaft to rotate with a gear, the gear is engaged with a rack and drives the entire sliding platform to move on the slide rail by means of pulleys, and the sliding platform arrives at a target position above the crop according to position and serial number of preset landmark sensor, and the movement in the travel direction stops; then the industrial PC sends an instruction to the DSP movement controller to drive a lifting mechanism, so as to lower the lifting mechanism of the sliding platform to a preset height; thus, the target positioning of the sliding platform is completed; the industrial PC sends a signal to the DSP movement controller to drive an electronically-controlled rotating head to adjust the tilt angle according to preset parameters, so as to ensure that the detection viewing field and detection angle of the multi-sensor system at the initial detection position meet the requirements for imaging and detection;

3.2) Detection of crop nutrition, water, growth and pest and disease information by point-by-point matrix gridding scanning:

The matrix scanning method described herein is as follows:

①  The industrial PC sends an instruction to the DSP movement controller to drive the electronically-controlled rotating head, so as to carry out point-by-point scanning from left to right in 0-180° arc direction, with a direction perpendicular to the travel direction as the X-axis and the geometric center of the electronically-controlled rotating head as the origin; at each detection position, the start point of detection in the travel direction is the initial point where the landmark sensor is detected and the sliding platform stops;

②  After the sequential detection is completed, step-scan the next are grid, wherein the step interval is set to a value between 10 mm and the maximum diameter of the plant crown width, to cover the entire plant crown layer, in that interval, perform are gridding scanning in the travel direction, and utilize a laser ranging sensor to acquire lattice information of height coordinate in the plant area by point scanning;

③  Whenever the scan reaches the center line of detection at 90° angle, utilize a binocular multi-functional imaging system to acquire a binocular vision top view image of the plant, a visible light characteristic image of the crown layer, and a near-infrared characteristic image of the crown layer;

④  At each detection position, when the scan reaches the geometric center of the plant, utilize an infrared temperature measurement sensor to acquire the crown layer temperature information of the crop, utilize a light intensity sensor to acquire the environmental light intensity information at the detection position, and utilize environmental temperature and humidity sensor to acquire the environmental temperature and humidity information at the detection position;

S4: Comprehensive Greenhouse Crop Information Processing

Upload the greenhouse crop information acquired in the step S3 to the industrial PC via an information acquisition module for processing, and a processing program processes the information according to the following method:

4.1) Information Processing of the Binocular Multi-Functional Imaging System

①  First, filter the visible light characteristic images of the crown layer and the near-infrared characteristic images of the crown layer acquired in the sub-step (3) in the step 3.2) with the binocular multi-functional imaging system to remove noise; then, carry out color space conversion and background segmentation for the images; finally, calculate the average values of texture and greyscale of the images to extract characteristic wavelengths of nitrogen, phosphorus, and potassium nutrition, water, and pests and diseases of the crop; utilize a crop growth information detection model to evaluate nitrogen, phosphorus and potassium contents, pest and disease types and water stress state;

②  Respectively calibrate and correct the left and right cameras for the binocular vision top view images acquired by the binocular multi-functional imaging system in the sub-step (3) in the step 3.2), and establish a world coordinate system; then carry out preprocessing for the images taken by the left and right cameras respectively; finally, carry out three-dimensional matching for the images, and establish a space coordinate system, to obtain plant height information;

③  Filter the information of the binocular vision top view images of the plant acquired by the binocular multi-functional imaging system in the sub-step (3) in the step 3.2 to remove noise and carry out background segmentation to obtain target images of the plant crown width; obtain the crown width area of the plant by counting the target pixels with reference to the scale data;

④  Screen and analyze sequential images of the geometric center line in the binocular vision top view image information of the plant obtained by the binocular multi-functional imaging system in the sub-step (3) in the step 3.2), select unshielded images of plant fruits and perform filtering to remove noise, carry out background segmentation, and obtain target images of plant fruits; then obtain the area value of the fruit area of the plant by counting the pixels of the target area;

4.2) Information Processing of Laser Ranging Sensor:

① Calibrate the lattice data of height coordinate of the plant area obtained by the laser ranging sensor in the step 3.2), determine the average height value of the planting substrate of the plant, and take the average height value as a starting point coordinate for calculation of plant height;

② Screen the lattice data of the height coordinate of the plant area obtained by the laser ranging sensor through gridding scanning in a matrix scan mode in the step 3.2) to remove redundant and invalid data;

③ Analyze the valid values in the lattice data of the height coordinate of the plant area obtained by the laser ranging sensor through gridding scanning in a matrix scan mode in the step 3.2) to obtain the highest point as the plant height data; obtain maximum boundary length, width and geometric center coordinates, and calibrate and calculate the area value of the crown width with reference to the measured values;

4.3) Fusion Detection of Comprehensive Greenhouse Crop Information

① Fusion detection of plant growth: based on the plant height, crown width area, and area value of fruit area extracted from the information acquired by the binocular multi-functional imaging system and the plant height and crown width information in the lattice area of the height coordinate obtained from the information acquired by the laser ranging sensor, after obtaining measured values of actual nitrogen, phosphorus and potassium contents by collecting crop leaves and carrying out chemical experiments, establish multi-variable linear regression, i.e., establish a regression model with the measured values of nitrogen, phosphorus and potassium as dependent variables and the plant height, crown width and fruit information extracted on the basis of binocular vision and the plant height and crown width information obtained by means of laser ranging in the lattice area of the height coordinate as independent variables, and perform correction for fusion of the two types of information; moreover, further correct the detection accuracy based on the measured value of growth, and extract fused values of plant height, crown width and fruit growth based on the characteristics of the binocular stereo vision images and the laser scanning lattice;

② Fusion detection of plant nutrition: establish multi-variable linear regression with the average values of texture and grayscale and characteristic wavelengths of nitrogen, phosphorus and potassium in the crop obtained on the basis of the visible light characteristic images of the crown layer and the near-infrared characteristic images of the crown layer acquired by the binocular multi-functional imaging system and the chemically measured values of nitrogen, phosphorus and potassium in the crop, i.e., establish a regression model with the chemically measured values of nitrogen, phosphorus and potassium as dependent variables and the average values of texture and greyscale and characteristic wavelengths as independent variables, and extract fused characteristic values of nitrogen, phosphorus and potassium nutrition in the crop on the basis of the characteristics of the visible light images and near-infrared images and the laser scanning lattice;

③ Fusion detection of plant water stress: establish multi-variable linear regression with the water content and average values of texture and greyscale of the crop obtained on the basis of the near-infrared characteristic images of the crown layer acquired by the binocular multi-functional imaging system, the characteristic value of water stress index based on the plant crown-air temperature difference acquired with the infrared temperature sensor and the environmental temperature and humidity sensor, and the measured value of water content in the crop, i.e., establish a regression model with the chemically measured values of nitrogen, phosphorus and potassium as dependent variables and the average values of texture and greyscale and characteristic wavelengths as independent variables; that is to say, establish a regression model with the measured value of water content as an dependent variable and the water stress index and average values of texture and greyscale of the near-infrared images as independent variables; extract fused characteristic value of water content in the crop on the basis of the characteristics of the near-infrared images, infrared temperature sensor, and environmental temperature and humidity sensor;

④ Detection of plant pests and diseases: extract characteristic leaves affected by diseases on the basis of the visible light characteristic images of the crown layer and the near-infrared characteristic images of the crown layer acquired by the binocular multi-functional imaging system, and identify the types and severities of the crop diseases with a disease classification model; based on the visible light characteristic images of the crown layer and the near-infrared characteristic images of the crown layer acquired by the binocular multi-functional imaging system, compared the differences in time-series images to judge the severity of pest occurrence, and make a warning judgment on outbreak of pests and diseases with reference to the environmental temperature and humidity and historical weather information;

⑤ Synchronously acquire the environmental lighting and temperature and humidity information in the greenhouse with the environmental light intensity sensor and the environmental temperature and humidity sensors, correct the detected characteristic values of comprehensive plant growth information, to eliminate the interferences of environmental factors on the detection results;

⑥ Take the detected values of greenhouse crop and environment information which have been subjected to interference correction as result output values, and display them on a touch screen, and import the detection results into a database;

S5: After the plant information acquisition is completed, the industrial PC sends an instruction to the DSP movement controller to drive the electronically-controlled head to rotate to the initial position and retract the lifting mechanism to the initial state according to preset route; the sliding platform travels to the next detection position according to a preset route; then the steps S5-S5 are repeated till the entire detection process is completed; then the sliding platform returns to the initial position.

Furthermore, in the step 2.3), the movement of the sliding platform is set on a basis that the crown layer area detected at the initial detection position should account for more than 70% of the viewing field area and the distance from the plant top to the sensor is between 500 mm and 1,000 mm for single plant detection.

Furthermore, in the step 4.2), the lattice data of height coordinate is filtered to remove redundant and invalid data under the following principle: for large-size crops, the height is valid if it is greater than 250 mm and smaller than 1,700 mm, and invalid data in the scanning process is removed on the basis of that threshold, for small-size crops and crops in the seedling stage, the height is valid if it is within a threshold interval of 20 mm-1,000 mm, and invalid data in the scanning process is removed on the basis of that threshold.

Furthermore, the near-infrared characteristic images of the crown layer are near-infrared characteristic images at 930 nm and 1,420 nm.

Beneficial Effects of the Present Invention (1) In the present invention, a mobile detection platform based on suspended slide rails is employed, a multi-sensor system is installed on the suspended sliding platform, and a lifting mechanism and an electronically-controlled rotating head are utilized; thus, not only accurate positioning and point-by-point detection in the travel direction of the detection can be realized, but also multi-sensor information cruise detection with different detection ranges, different top-view viewing fields, and different detection angles can be realized. The method provided in the present invention not only can perform detection for large-size plants such as tomatoes and cucumbers, etc., but also can meet the detection requirements for lettuce and medium-size and small-size plants in different growing stages.

(2) In the present invention, a binocular vision multi-functional camera is employed, and a matrix gridding scanning method is used through a laser ranging sensor, so as to acquire binocular 3D visual images of the plants and a laser-ranging height coordinate lattice, and fusion correction is carried out on the basis of the plant height, crown width and fruit information of the plants extracted on the basis of binocular vision and the plant height and crown width information of the plants in a lattice area of the height coordinate acquired by laser ranging, so as to realize accurate detection of the growth of the plants in the greenhouse.

(3) In the present invention, a binocular vision multi-functional camera is employed, and a visible light imaging device based on a front optical filter set is utilized to acquire characteristic images of the plant crown layer at 472 nm, 556 nm, and 680 nm, and in combination with analysis on the gridding scanning imaging of a multi-sensor system and the step sequence and time sequence imaging, through multi-information fusion, the identification and diagnosis of information on nitrogen, phosphorus and potassium nutrition stress and pests and diseases of the plants can be realized.

(4) In the present invention, a binocular vision multi-functional camera is employed and an near-infrared imaging device based on a front optical filter set is utilized to acquire characteristic images of water stress in the plants at 930 nm and 1,420 nm, and, with the crown-air temperature difference characteristic of water stress of the plant obtained by detecting the infrared temperature of the crown layer and the environmental temperature and humidity, accurate identification and detection of the water stress state of the plants in the greenhouse can be realized through fusion correction of the information.

(5) In the present invention, error compensation is carried out for the acquired multi-sensor characteristics of the crops in the greenhouse with the crown layer light intensity and environmental temperature information in the greenhouse acquired synchronously, so as to effectively eliminate the error influences of lighting and environmental changes on detection results and further improve the detection accuracy.

(6) The suspended automatic cruise detection platform employed in the present invention can carry out on-line and timing cruise monitoring of comprehensive information of crops and the environment in the entire greenhouse, and provides a scientific basis for regulation and management of water, fertilizer, and environment in the greenhouse, and can greatly reduce the input of detecting equipment and personnel, effectively avoid manual operating errors, and improve the detection accuracy and working efficiency of environment and plant growth information in the greenhouse, when compared with traditional artificial experience and distributed monitoring systems.

IV. DESCRIPTION OF DRAWINGS

1—slide rail; 2—main suspension beam; 3—auxiliary suspension beam; 4—toothed rack; 5—cross brace; 6—rail connecting plate; 7—gear rack A; 8—gear rack B; 9—deceleration motor; 10—gear shaft; 11—gear; 12—bearing; 13—photoelectric encoder, 14—pulley; 15—DSP movement controller, 16—power supply of the lifting mechanism; 17—terminal limit switch; 18—suspension; 19—lifting mechanism; 20—lifting coiled strip; 21—electronically-controlled rotating head; 22-1—visible light multi-function imaging system; 22-2—near-infrared multi-function imaging system; 23-1—sensor bracket A; 23-2—sensor bracket B; 24—head bracket; 25—infrared temperature measurement sensor, 26—temperature and humidity sensor, 27—laser ranging sensor, 28—light intensity sensor, 29—control cabinet body; 30—touch display screen; 31—power supply of the display screen; 32—industrial PC; 33—power supply of the industrial PC; 34—power socket; 35—cultivation tank; 36—landmark sensor; 37—plant; 38—grid scanning trajectory of multi-sensor system

V. EMBODIMENTS

The following is a further detailed description of the invention in combination with the attached drawings.

Figure 1:
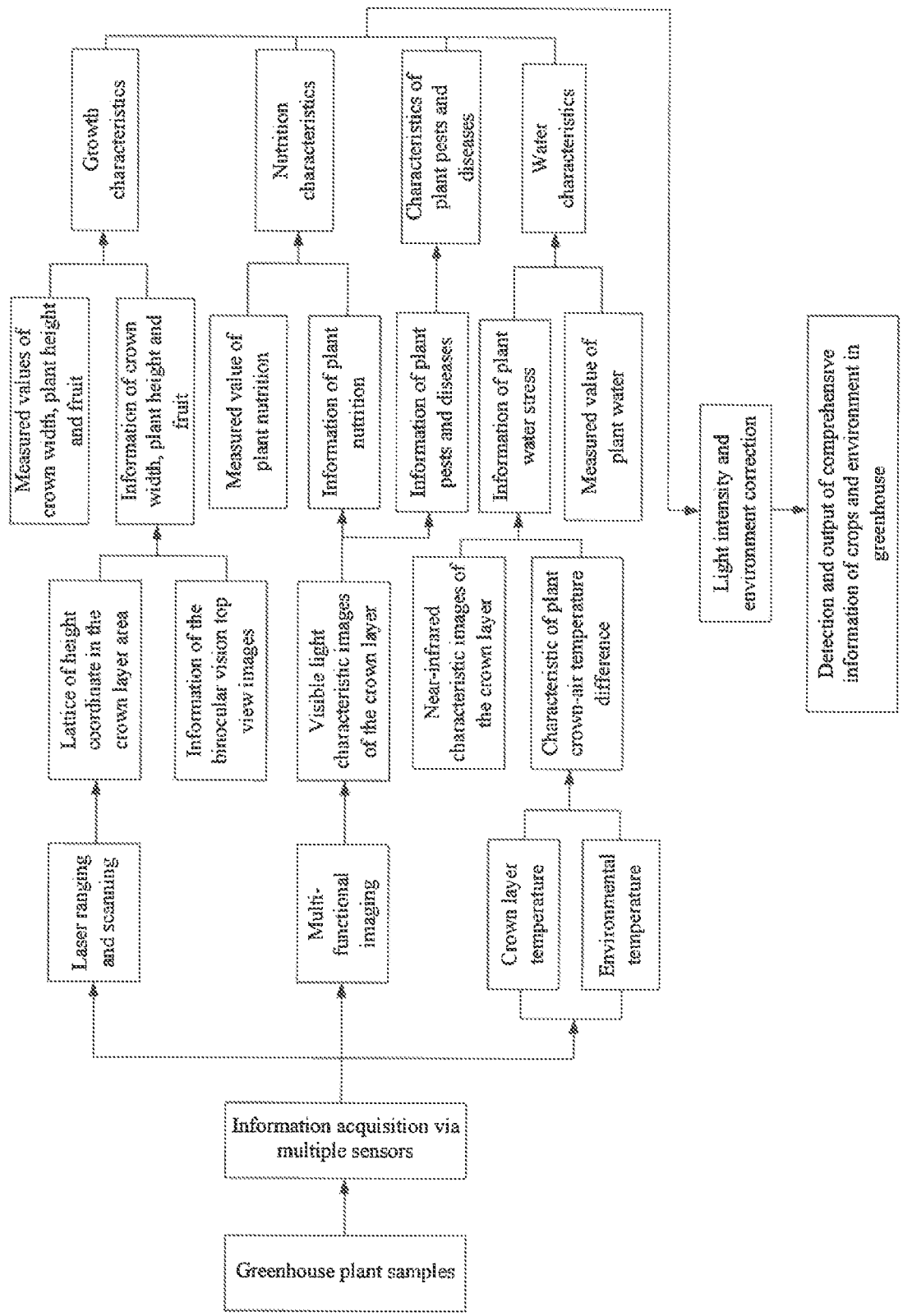
FIG. 1 is a flow chart of greenhouse information automatic monitoring and multi-sensor detection method based on the suspended slide rail platform.
Figure 8:
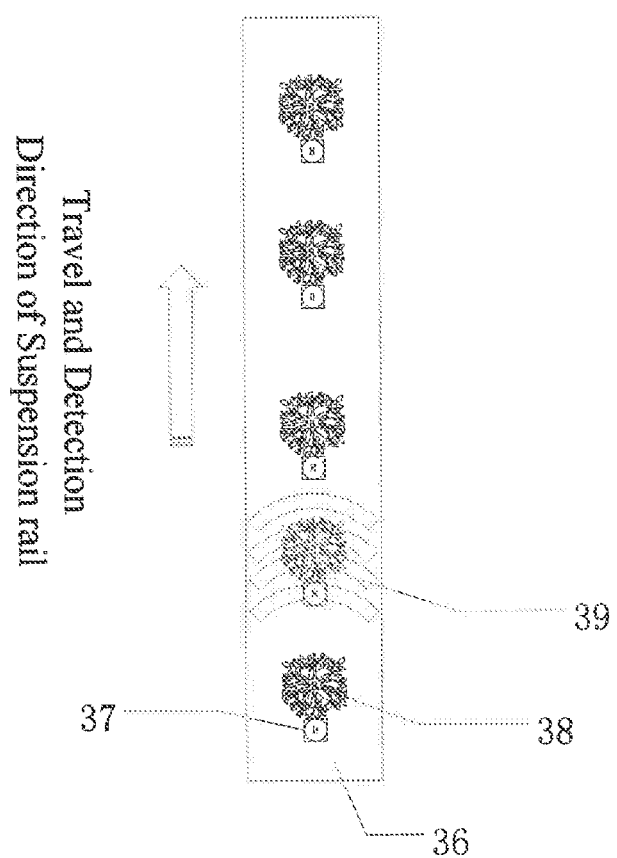
FIG. 8 is a schematic diagram of sensor grid scanning of the automatic monitoring method.

As shown in FIG. 1, the greenhouse crop information automatic monitoring method described in the present invention is based on a suspended slide platform, including the following steps:

S1: System Initialization:

Press the power button in a control cabinet to start up a monitoring system for comprehensive greenhouse information based on a suspended slide rail platform and let the system perform self-check, start up an industrial PC 32 and switch on a touch display screen 30, start up a DSP movement controller 15 and let a sliding platform return to zero position;

S2: System Setting:

2.1) Sample setting and sampling interval setting: set a plant spacing of the plants 37 to be measured, and set landmarks 36, a movement interval of the sliding platform, and a sampling interval of a multi-sensor system;

Since this system can be applied to different types of facility crops, the type, planting time and growing period of crops should be firstly set with touch display screen 30. Since this system adopts the working mode of individual plant detection, the planting distance of plant 37 to be tested in the cultivation tank 35 set by touch display screen 30 should be used first, and the movement distance of landmark sensor 36, sliding platform and sampling distance of multi-sensor system should be set accordingly, as shown in FIG. 8.

2.2) Detection parameter setting: set detection modes and detection parameters, wherein the detection modes include four modes: crop nutrition stress detection, pest and disease detection, water stress detection and growth detection; wherein the parameter setting includes: nitrogen, phosphorus and potassium detection in the nutrition stress mode, species identification in the pest and disease detection mode, and plant height, crown width and fruits in the growth detection mode;

2.3) Sliding platform movement setting: set movement route and detection height of the sliding platform according to the detection parameters, crop growth period and species;

According to different testing parameters, crop growth period and type selection of sports, the crop seedling stage or the small plant crops such as lettuce, can choose low detection, for a large plant crops such as tomatoes and cucumbers, adopt high detection, selection is based on individual test, the initial testing and detection of canopy area accounts for the area of the field area should be more than 70%, at the same time of top distance sensor distance between 500 mm to 1000 mm, if does not meet the need to replace the imaging lens to meet the requirements of the above parameters.

S3: Crop information detection: After the setup process, the system sends instructions to DSP movement controller 15 and multi-sensor system through the industrial PC 32. Probing procedures for motion control and crop nutrition, moisture, growth and pest information in accordance with established testing procedures. first, the DSP movement controller 15 sends a signal to a deceleration motor 9 according to a position instruction sent from the industrial PC 32, the deceleration motor 9 drives a gear 10 shaft to rotate with a gear 10, the gear 11 is engaged with a rack 14 and drives the entire sliding platform to move on the slide rail 1 by means of pulleys 14, and the sliding platform arrives at a target position above the crop according to position and serial number of preset landmark sensor 36. Detection of crop nutrition, water, growth and pest and disease information by point-by-point matrix gridding scanning. The matrix scanning method described herein is as follows:

3.1) Target Positioning of the Sliding Platform

According to the sampling interval set in 2.1), first, the DSP movement controller sends a signal to a deceleration motor according to a position instruction sent from the industrial PC, the deceleration motor drives a gear shaft to rotate with a gear, the gear is engaged with a rack and drives the entire sliding platform to move on the slide rail by means of pulleys, and the sliding platform arrives at a target position above the crop according to position and serial number of preset landmark sensor, and the movement in the travel direction stops; then the industrial PC sends an instruction to the DSP movement controller to drive a lifting mechanism, so as to lower the lifting mechanism of the sliding platform to a preset height; thus, the target positioning of the sliding platform is completed; the industrial PC sends a signal to the DSP movement controller to drive an electronically-controlled rotating head to adjust the tilt angle according to preset parameters, so as to ensure that the detection viewing field and detection angle of the multi-sensor system at the initial detection position meet the requirements for imaging and detection;

3.2) Detection of Crop Nutrition, Water, Growth and Pest and Disease Information by Point-by-Point Matrix Gridding Scanning:

the target positioning of the sliding platform is completed; the industrial PC sends a signal to the DSP movement controller to drive an electronically-controlled rotating head to adjust the tilt angle according to preset parameters, so as to ensure that the detection viewing field and detection angle of the multi-sensor system at the initial detection position meet the requirements for imaging and detection; Detection of crop nutrition, water, growth and pest and disease information by point-by-point matrix gridding scanning:

The matrix scanning method described herein is as follows:

(1) The industrial PC 32 sends an instruction to the DSP movement controller 15 to drive the electronically-controlled rotating head 21, so as to carry out point-by-point scanning from left to right in 0-180° arc direction, with a direction perpendicular to the travel direction as the X-axis and the geometric center of the electronically-controlled rotating head 21 as the origin; at each detection position, the start point of detection in the travel direction is the initial point where the landmark sensor 36 is detected and the sliding platform stops;

(2) After the sequential detection is completed, step-scan the next arc grid, wherein the step interval is set to a value between 10 mm and the maximum diameter of the plant crown width, to cover the entire plant crown layer, in that interval, perform arc gridding scanning 38 in the travel direction, and utilize a laser ranging sensor 27 to acquire lattice information of height coordinate in the plant area by point scanning;

(3) Whenever the scan reaches the center line of detection at 90° angle, utilize a binocular multi-functional imaging system 22 to acquire a binocular vision top view image of the plant, a visible light characteristic image of the crown layer, and a near-infrared characteristic image of the crown layer;

(4) At each detection position, when the scan reaches the geometric center of the plant, utilize an infrared temperature measurement sensor 25 to acquire the crown layer temperature information of the crop, utilize a light intensity sensor 28 to acquire the environmental light intensity information at the detection position, and utilize environmental temperature and humidity sensor 26 to acquire the environmental temperature and humidity information at the detection position;

S4: Comprehensive Greenhouse Crop Information Processing

Upload the greenhouse crop information acquired in the step S3 to the industrial PC via an information acquisition module for processing, and a processing program processes the information according to the following method:

4.1) Information Processing of the Binocular Multi-Functional Imaging System (5) First, filter the visible light characteristic images of the crown layer and the near-infrared characteristic images of the crown layer acquired in the sub-step (3) in the step 3.2) with the binocular multi-functional imaging system to remove noise; then, carry out color space conversion and background segmentation for the images; finally, calculate the average values of texture and greyscale of the images to extract characteristic wavelengths of nitrogen, phosphorus, and potassium nutrition, water, and pests and diseases of the crop; utilize a crop growth information detection model to evaluate nitrogen, phosphorus and potassium contents, pest and disease types and water stress state;

(6) Respectively calibrate and correct the left and right cameras for the binocular vision top view images acquired by the binocular multi-functional imaging system 22 in the sub-step (3) in the step 3.2), and establish a world coordinate system; then carry out preprocessing for the images taken by the left and right cameras respectively; finally, carry out three-dimensional matching for the images, and establish a space coordinate system, to obtain plant height information;

(7) Filter the information of the binocular vision top view images of the plant acquired by the binocular multi-functional imaging system 22 in the sub-step (3) in the step 3.2 to remove noise and carny out background segmentation to obtain target images of the plant crown width; obtain the crown width area of the plant by counting the target pixels with reference to the scale data;

(8) Screen and analyze sequential images of the geometric center line in the binocular vision top view image information of the plant obtained by the binocular multi-functional imaging system 22 in the sub-step (3) in the step 3.2), select unshielded images of plant fruits and perform filtering to remove noise, carry out background segmentation, and obtain target images of plant fruits; then obtain the area value of the fruit area of the plant by counting the pixels of the target area.

4.2) Information Processing of Laser Ranging Sensor.

④ Calibrate the lattice data of height coordinate of the plant area obtained by the laser ranging sensor 27 in the step 3.2), determine the average height value of the planting substrate of the plant, and take the average height value as a starting point coordinate for calculation of plant height;

⑤ Screen the lattice data of the height coordinate of the plant area obtained by the laser ranging sensor 27 through gridding scanning in a matrix scan mode in the step 3.2) to remove redundant and invalid data; the lattice data of height coordinate is filtered to remove redundant and invalid data under the following principle: For tomato cucumber and other large plant type crops, the height is valid if it is greater than 250 mm and smaller than 1,700 mm, and invalid data in the scanning process is removed on the basis of that threshold; for small-size crops and crops in the seedling stage, the height is valid if it is within a threshold interval of 20 mm-1,000 mm, and invalid data in the scanning process is removed on the basis of that threshold.

⑥ Analyze the valid values in the lattice data of the height coordinate of the plant area obtained by the laser ranging sensor 27 through gridding scanning in a matrix scan mode in the step 3.2) to obtain the highest point as the plant height data; obtain maximum boundary length, width and geometric center coordinates, and calibrate and calculate the area value of the crown width with reference to the measured values;

4.3) Fusion Detection of Comprehensive Greenhouse Crop Information

① Fusion detection of plant growth: based on the plant height, crown width area, and area value of fruit area extracted from the information acquired by the binocular multi-functional imaging system and the plant height and crown width information in the lattice area of the height coordinate obtained from the information acquired by the laser ranging sensor, after obtaining measured values of actual nitrogen, phosphorus and potassium contents by collecting crop leaves and carrying out chemical experiments, establish multi-variable linear regression, i.e., establish a regression model with the measured values of nitrogen, phosphorus and potassium as dependent variables and the plant height, crown width and fruit information extracted on the basis of binocular vision and the plant height and crown width information obtained by means of laser ranging in the lattice area of the height coordinate as independent variables, and perform correction for fusion of the two types of information; moreover, further correct the detection accuracy based on the measured value of growth, and extract fused values of plant height, crown width and fruit growth based on the characteristics of the binocular stereo vision images and the laser scanning lattice;

⑤ Fusion detection of plant nutrition: establish multi-variable linear regression with the average values of texture and grayscale and characteristic wavelengths of nitrogen, phosphorus and potassium in the crop obtained on the basis of the visible light characteristic images of the crown layer and the near-infrared characteristic images of the crown layer acquired by the binocular multi-functional imaging system and the chemically measured values of nitrogen, phosphorus and potassium in the crop, i.e., establish a regression model with the chemically measured values of nitrogen, phosphorus and potassium as dependent variables and the average values of texture and greyscale and characteristic wavelengths as independent variables, and extract fused characteristic values of nitrogen, phosphorus and potassium nutrition in the crop on the basis of the characteristics of the visible light images and near-infrared images and the laser scanning lattice;

③ Fusion detection of plant water stress: establish multi-variable linear regression with the water content and average values of texture and greyscale of the crop obtained on the basis of the near-infrared characteristic images of the crown layer acquired by the binocular multi-functional imaging system 22, the characteristic value of water stress index based on the plant crown-air temperature difference acquired with the infrared temperature sensor and the environmental temperature and humidity sensor, and the measured value of water content in the crop, i.e., establish a regression model with the chemically measured values of nitrogen, phosphorus and potassium as dependent variables and the average values of texture and greyscale and characteristic wavelengths as independent variables; that is to say, establish a regression model with the measured value of water content as an dependent variable and the water stress index and average values of texture and greyscale of the near-infrared images as independent variables; extract fused characteristic value of water content in the crop on the basis of the characteristics of the near-infrared images, infrared temperature sensor, and environmental temperature and humidity sensor;

④ Detection of plant pests and diseases: extract characteristic leaves affected by diseases on the basis of the visible light characteristic images of the crown layer and the near-infrared characteristic images of the crown layer acquired by the binocular multi-functional imaging system, and identify the types and severities of the crop diseases with a disease classification model; based on the visible light characteristic images of the crown layer and the near-infrared characteristic images of the crown layer acquired by the binocular multi-functional imaging system, compared the differences in time-series images to judge the severity of pest occurrence, and make a warning judgment on outbreak of pests and diseases with reference to the environmental temperature and humidity and historical weather information;

⑤ Synchronously acquire the environmental lighting and temperature and humidity information in the greenhouse with the environmental light intensity sensor and the environmental temperature and humidity sensors, correct the detected characteristic values of comprehensive plant growth information, to eliminate the interferences of environmental factors on the detection results;

⑥ Take the detected values of greenhouse crop and environment information which have been subjected to interference correction as result output values, and display them on a touch screen, and import the detection results into a database;

S5: After the plant information acquisition is completed, the industrial PC 32 sends an instruction to the DSP movement controller 15 to drive the electronically-controlled head 21 to rotate to the initial position and retract the lifting mechanism 19 to the initial state according to preset route; the sliding platform travels to the next detection position according to a preset route; then the steps S3-S5 are repeated till the entire detection process is completed; then the sliding platform returns to the initial position.

Figure 2:
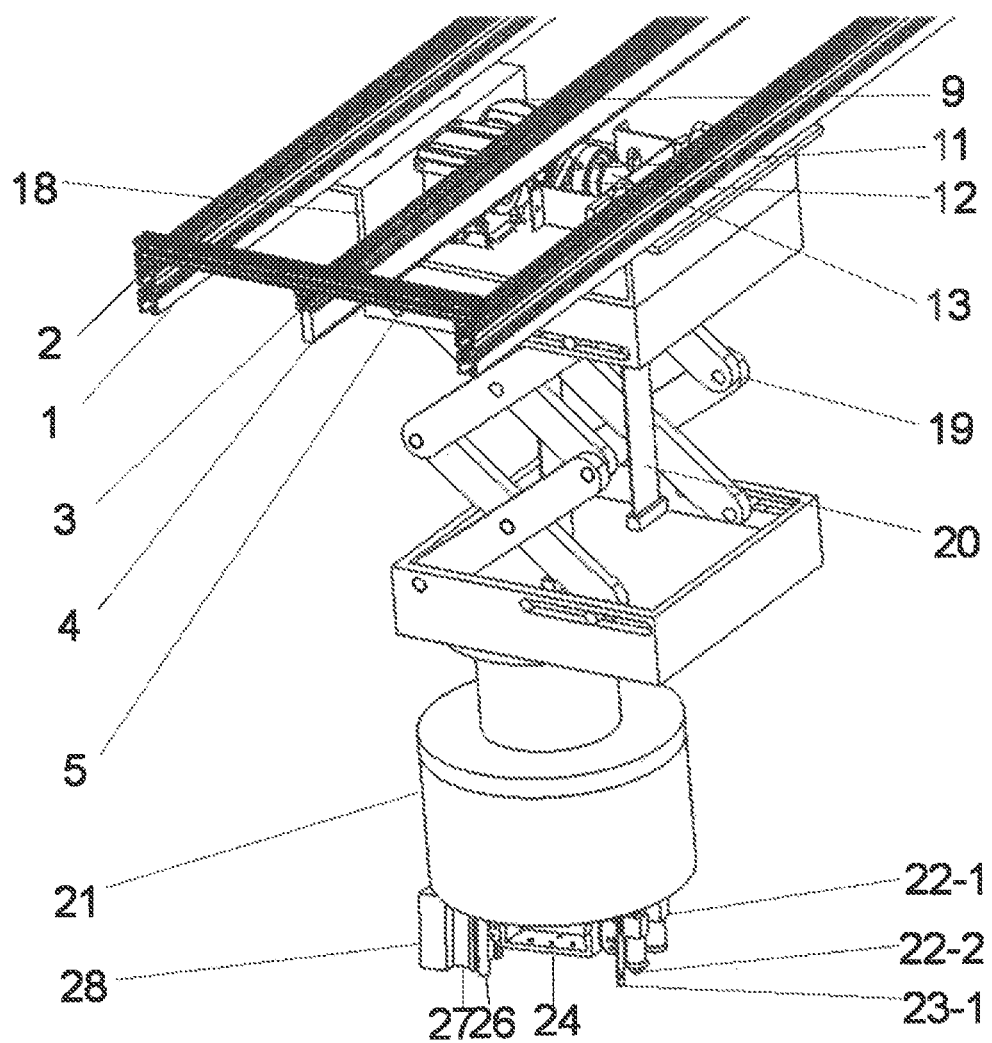
FIG. 2 is a schematic diagram of the overall structure of the suspended rail-type automatic cruise monitoring device for comprehensive greenhouse information.

The greenhouse information automatic monitoring method based on the suspended sliding rail platform is realized by the greenhouse comprehensive information automatic cruise monitoring device based on the suspended sliding rail platform. The suspension rail greenhouse comprehensive information automatic cruise monitoring device includes rail assembly, walking mechanism, sliding platform, multi-sensor system and control cabinet assembly, as shown in FIG. 2.

Figure 3:
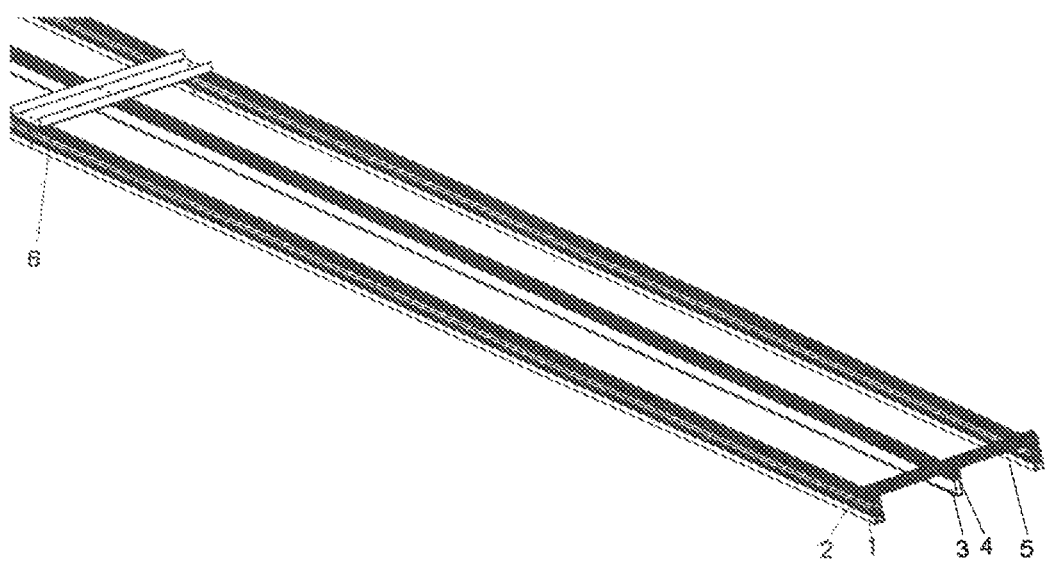
FIG. 3 is a schematic structural diagram of the track assembly.

As shown in FIG. 3, the track assembly mainly consists of sliding rails 1 and rack 4, respectively fixed on the cross structural beam of the greenhouse. Specifically, the left middle right three parts of the track assembly are composed; The sliding track 1 is fixed below the hanging main beam 2 and is the sliding track of the sliding platform and walking mechanism. The slip track 1 of the left and right parts is fixed on the left and right suspended main beams 2. The left and right suspended main beams 2 are parallel structures with an interval of 700 mm. The length of the left and right main beams is 18 meters, and they are respectively composed of 3 aluminum profiles with a length of 6 meters, 30×60. The left and right sliding track 1 has the same length of 18 meters and is composed of 3 stainless steel tracks 6 meters long respectively. The sliding track 1 length is tightly connected with the hanging main beam 2 every 500 mm through t-bolt and nut. In the parallel middle line with the suspension main beam 2, the suspension auxiliary beam 3 is installed, the suspension auxiliary beam 3 is composed of 3 30×30 aluminum profiles with a length of 6 meters, the bottom of which is fixed by T screw with rack 4, rack 4 is 18 meters long, and is composed of 6 rack fixed connections with a length of 3 meters.

In order to maintain straightness and structural stiffness between the suspended main beam 2 and the suspended auxiliary beam 3, in the direction of track length, the transverse brace 5 is used every 500 mm to tighten and connect the main beam 2 and the suspended auxiliary beam 3 through t-shaped bolts and nuts, so that the suspended main beam 2 and the suspended auxiliary beam 3 become an integral whole to ensure the structural stiffness. At the joints where the 6-meter profiles used for hanging main beam 2 and hanging auxiliary beam 3 are connected, the connecting plate 6 is used to tighten the connection between the suspended main beam 2 and the suspended auxiliary beam 3 through t-shaped bolts and nuts, so as to ensure the smooth transition of the sliding platform along the sliding track 1 at the joints.

Figure 4:
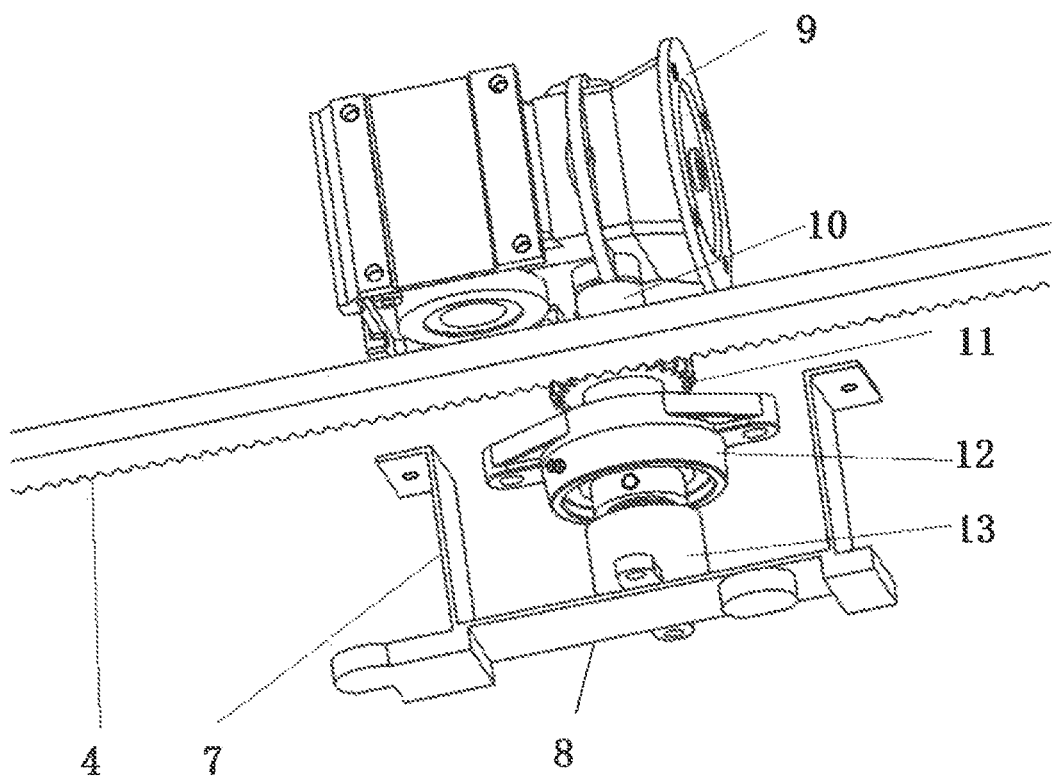
FIG. 4 is a schematic structural diagram of the travelling mechanism.

The walking mechanism is shown in FIG. 4. The walking mechanism is composed of rack 4, gear rack A7, gear rack B8, reduction motor 9, gear shaft 10, gear 11, bearing 12 and photoelectric encoder 13. The reduction motor 9 is connected with the gear shaft 10 through the spline on the shaft. Bearing 12 is connected to gear frame A7 through bolts and nuts. Gear rack A7 and gear rack A8 are connected by bolts and nuts; The photoelectric encoder 13 is connected to the gear shaft 10 through the top wire on the shaft to realize the calculation and detection of travel distance and position. The traveling mechanism is connected with the sliding track 1 and rack 4 of the track assembly to form a set of rack and pinion mechanism and a set of slide track mechanism.

Figure 5:
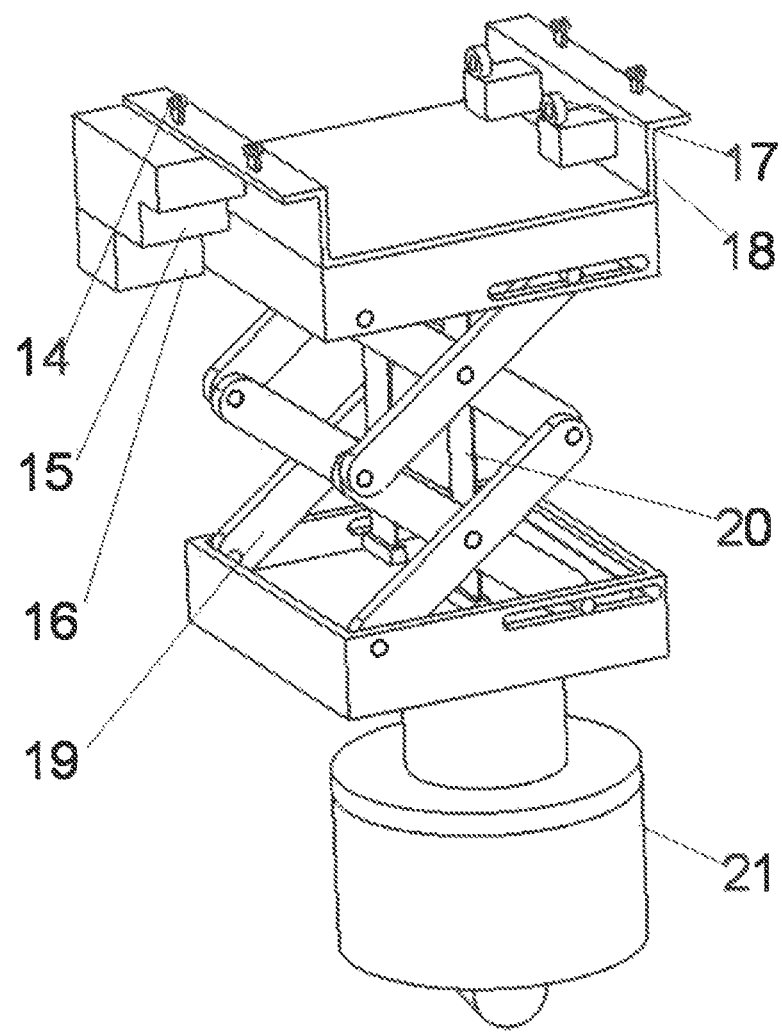
FIG. 5 is a schematic structural diagram of the sliding platform.

The main body of the sliding platform is driven by a walking mechanism, as shown in FIG. 5. The sliding platform is composed of 4 groups of pulleys 14, terminal limit switch 17, suspension 18, lifting mechanism 19, electrically controlled rotating head 21, lifting mechanism power 16 and DSP motion controller 15. Pulley 14 and suspension 18 are connected as a whole through bolts and suspended in the chute of slide rail 1, which can slide along the length direction of slide rail 1 as a whole with pulley 14. The lifting mechanism 19 and suspension 18 are fastened together with the base and suspension 18 by bolts and nuts; Lifting mechanism for the shear knife and fork telescopic mechanism, by controlling the lifting coil with 20 telescopic, to achieve the sliding platform lifting operation, in order to facilitate the multi-sensor system for the best height detection bit up and down adjustment. The terminal limit switch 17 of the front and rear moving directions is fixed on the top of the suspension 18 with t-screw along the two end positions of the front and rear moving directions. When the equipment runs to the end, the front end of the limit block touches the terminal limit switch 17 to make the whole system power off and brake.

Electrically controlled rotating head 21 and the bottom of lifting mechanism 19 are connected by bolts and nuts; The lifting mechanism power supply 16, DSP motion controller 15, signal connection and other communication devices are fixed on the sliding platform and fixed on the moving direction end face of the lifting mechanism 19 by bolts and nuts. DSP motion controller 15 can realize the control of movement and lifting of the sliding platform before and after movement. Multi-sensor system in electrically controlled rotating head 21 below, via electrically controlled rotating head 21 the multi-sensor was driven to implement horizontal rotation of 360° and vertical rotation of 180°, cooperated with the lifting mechanism, under the drive control of DSP motion controller 15, can satisfy different detection range, overlooking the view, the different Angle of multi-sensor detecting demand.

Figure 6:
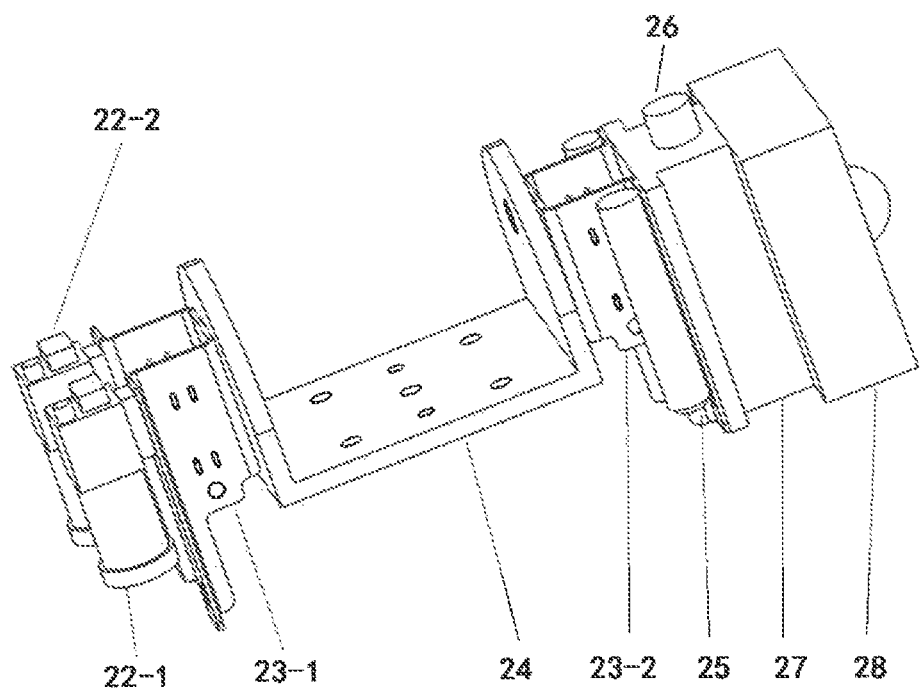
FIG. 6 is a schematic diagram of the multi-sensor system.

As shown in FIG. 6, the multi-sensor system includes light intensity sensor 28, laser ranging sensor 27, infrared temperature sensor 25, temperature and humidity sensor 26, and binocular multi-function imaging system. Sensor bracket a23-1 and sensor bracket b23-2 are respectively installed on both sides of the cradle holder 24 at the lower end of the electrically controlled rotating cradle holder 21. The binocular multifunctional imaging system includes the visible light multifunctional imaging system 22-1 and the near-infrared multifunctional imaging system 22-2, which is fixed on the sensor bracket a23-1 with the field of view downward. The front end of the visible light multifunctional imaging system 22-1 is equipped with a set of pre-visible light filters including 556 nm, 472 nm and 680 nm filters, which can achieve the acquisition of image information of crop nutrition characteristics. The front end of the NIR (Near-Infrared) multifunctional imaging system 22-2 is equipped with a group of front NIR filters including 930 nm and 1420 nm filters, which can achieve the acquisition of characteristic image information of crop water stress. At the same time, visible light multifunctional imaging system 22-1 and near-infrared multifunctional imaging system 22-2 can be used as multiplexing cameras to perform binocular visual matching, achieve stereoscopic imaging, and achieve the measurement of plant height and crown width area. The infrared temperature sensor 25, temperature and humidity sensor 26, laser ranging sensor 27 and light intensity sensor 28 are fixed on both sides of the sensor bracket b23-2, with the top view position and the detection direction vertically downward.

Figure 7:
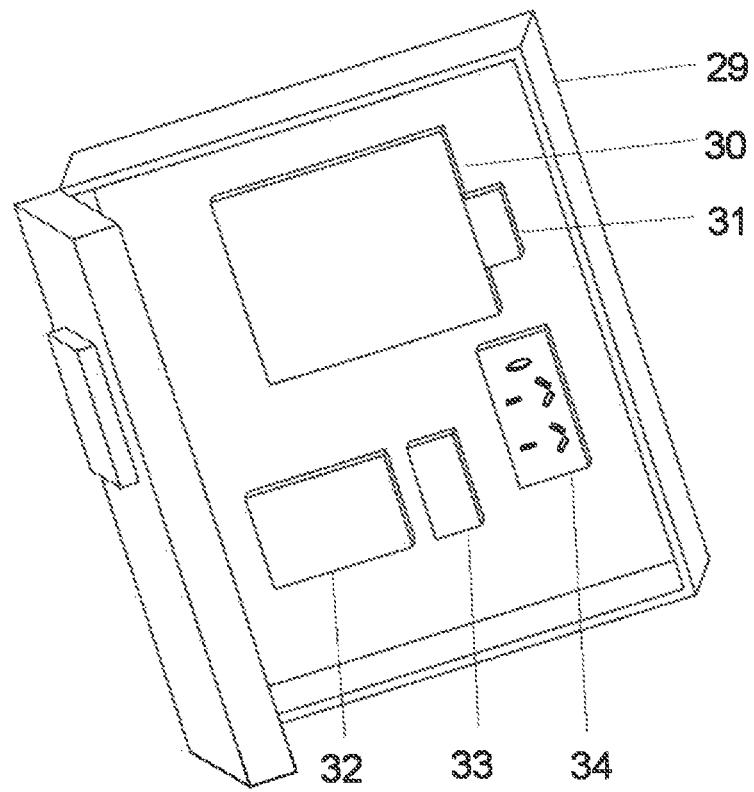
FIG. 7 is a schematic structural diagram of the control cabinet.

The control cabinet is independently fixed at the front of the greenhouse. As shown in FIG. 7, the control cabinet assembly consists of touch screen 30, display screen power 31, IPC (Industrial Process Control) 32, IPC power 33, power socket 34 and control cabinet main body 29. The control cabinet is connected to the walking mechanism, sliding platform and multi-sensor system respectively through 1394 data line for information interaction. The control cabinet provides power to the walking mechanism, sliding platform and multi-sensor system through the power cord.

While some preferred embodiments of the present invention are described above, the present invention is not limited to those embodiments. Any obvious improvement, replacement, or variation that can be made by those skilled in the art without departing from the spirit of the present invention shall be deemed as falling in the protection scope of the present invention.

The invention claimed is:

1. An automatic monitoring method for greenhouse crop information based on a suspended slide rail platform, comprising the following steps:

S1: System Initialization:
start up a monitoring system for comprehensive greenhouse information based on a suspended slide rail platform and let the system perform self-check, start up a PC and switch on a touch display screen, start up a DSP movement controller and let a sliding platform return to zero position;

S2: System Setting:
2.1) sample setting and sampling interval setting: set a plant spacing of the plants to be measured, and set landmarks, a movement interval of the sliding platform, and a sampling interval of a multi-sensor system;

2.2) detection parameter setting: set detection modes and detection parameters, wherein the detection modes include four modes: crop nutrition stress detection, pest and disease detection, water stress detection and growth detection; wherein the parameter setting includes: nitrogen, phosphorus and potassium detection in the nutrition stress mode, species identification in the pest and disease detection mode, and plant height, crown width and fruits in the growth detection mode;

2.3) sliding platform movement setting: set movement route and detection height of the sliding platform according to the detection parameters, crop growth period and species;

S3: Crop Information Detection:
3.1) target positioning of the sliding platform:
according to the sampling interval set in 2.1), first, the DSP movement controller sends a signal according to a position instruction sent from the PC to drive the entire sliding platform to move on the slide rail, and the sliding platform arrives at a target position above the crop according to position and serial number of preset landmark sensor, and the movement in the travel direction stops; then the PC sends an instruction to the DSP movement controller to drive a lifting mechanism, so as to lower the lifting mechanism of the sliding platform to a preset height; thus, the target positioning of the sliding platform is completed; the PC sends a signal to the DSP movement controller to drive an electronically-controlled rotating head to adjust the tilt angle according to preset parameters, so as to ensure that the detection viewing field and detection angle of the multi-sensor system at the initial detection position meet the requirements for imaging and detection;

3.2) detection of crop nutrition, water, growth and pest and disease information by point-by-point matrix gridding scanning:
the matrix scanning method described herein is as follows:

(1) the PC sends an instruction to the DSP movement controller to drive the electronically-controlled rotating head, so as to carry out point-by-point scanning from left to right in 0-180° arc direction, with a direction perpendicular to the travel direction as the X-axis and the geometric center of the electronically-controlled rotating head as the origin; at each detection position, the start point of detection in the travel direction is the initial point where the landmark sensor is detected and the sliding platform stops;

(2) after the sequential detection is completed, step-scan the next arc grid, wherein the step interval is set to a value between 10 mm and the maximum diameter of the plant crown width, to cover the entire plant crown layer; in that interval, perform arc gridding scanning in the travel direction, and utilize a laser ranging sensor to acquire lattice information of height coordinate in the plant area by point scanning;

(3) whenever the scan reaches the center line of detection at 90° angle, utilize a binocular multi-functional imaging system to acquire a binocular vision top view image of the plant, a visible light characteristic image of the crown layer, and a near-infrared characteristic image of the crown layer;

(4) at each detection position, when the scan reaches the geometric center of the plant, utilize an infrared temperature measurement sensor to acquire the crown layer temperature information of the crop, utilize a light intensity sensor to acquire the environmental light intensity information at the detection position, and utilize environmental temperature and humidity sensor to acquire the environmental temperature and humidity information at the detection position;

S4: Comprehensive Greenhouse Crop Information Processing:
upload the greenhouse crop information acquired in the step S3 to the PC via an information acquisition module for processing, and a processing program processes the information according to the following method:

4.1) information processing of the binocular multi-functional imaging system:

(1) first, filter the visible light characteristic images of the crown layer and the near-infrared characteristic images of the crown layer acquired in the sub-step ③ in the step 3.2) with the binocular multi-functional imaging system to remove noise; then, carry out color space conversion and background segmentation for the images; calculate the average values of texture and greyscale of the images to extract characteristic wavelengths of nitrogen, phosphorus, and potassium nutrition, water, and pests and diseases of the crop; utilize a crop growth information detection model to evaluate nitrogen, phosphorus and potassium contents, pest and disease types and water stress state;

(2) respectively calibrate and correct the left and right cameras for the binocular vision top view images acquired by the binocular multi-functional imaging system in the sub-step (3) in the step 3.2), and establish a world coordinate system; then carry out preprocessing for the images taken by the left and right cameras respectively; carry out three-dimensional matching for the images, and establish a space coordinate system, to obtain plant height information;

(3) filter the information of the binocular vision top view images of the plant acquired by the binocular multi-functional imaging system in the sub-step (3) in the step 3.2 to remove noise and carry out background segmentation to obtain target images of the plant crown width; obtain the crown width area of the plant by counting the target pixels with reference to the scale data;

(4) screen and analyze sequential images of the geometric center line in the binocular vision top view image information of the plant obtained by the binocular multi-functional imaging system in the sub-step (3) in the step 3.2), select unshielded images of plant fruits and perform filtering to remove noise, carry out background segmentation, and obtain target images of plant fruits; then obtain the area value of the fruit area of the plant by counting the pixels of the target area;

4.2) information processing of laser ranging sensor:

(1) calibrate the lattice data of height coordinate of the plant area obtained by the laser ranging sensor in the step 3.2), determine the average height value of the planting substrate of the plant, and take the average height value as a starting point coordinate for calculation of plant height;

(2) screen the lattice data of the height coordinate of the plant area obtained by the laser ranging sensor through gridding scanning in a matrix scan mode in the step 3.2) to remove redundant and invalid data;

(3) analyze the valid values in the lattice data of the height coordinate of the plant area obtained by the laser ranging sensor through gridding scanning in a matrix scan mode in the step 3.2) to obtain the highest point as the plant height data; obtain maximum boundary length, width and geometric center coordinates, and calibrate and calculate the area value of the crown width with reference to the measured values;

4.3) fusion detection of comprehensive greenhouse crop information:

(1) fusion detection of plant growth: based on the plant height, crown width area, and area value of fruit area extracted from the information acquired by the binocular multi-functional imaging system and the plant height and crown width information in the lattice area of the height coordinate obtained from the information acquired by the laser ranging sensor, after obtaining measured values of actual nitrogen, phosphorus and potassium contents by collecting crop leaves and carrying out chemical experiments, establish multi-variable linear regression, i.e., establish a regression model with the measured values of nitrogen, phosphorus and potassium as dependent variables and the plant height, crown width and fruit information extracted on the basis of binocular vision and the plant height and crown width information obtained by means of laser ranging in the lattice area of the height coordinate as independent variables, and perform correction for fusion of the two types of information; moreover, further correct the detection accuracy based on the measured value of growth, and extract fused values of plant height, crown width and fruit growth based on the characteristics of the binocular stereo vision images and the laser scanning lattice;

(2) fusion detection of plant nutrition: establish multi-variable linear regression with the average values of texture and grayscale and characteristic wavelengths of nitrogen, phosphorus and potassium in the crop obtained on the basis of the visible light characteristic images of the crown layer and the near-infrared characteristic images of the crown layer acquired by the binocular multi-functional imaging system and the chemically measured values of nitrogen, phosphorus and potassium in the crop, i.e., establish a regression model with the chemically measured values of nitrogen, phosphorus and potassium as dependent variables and the average values of texture and greyscale and characteristic wavelengths as independent variables, and extract fused characteristic values of nitrogen, phosphorus and potassium nutrition in the crop on the basis of the characteristics of the visible light images and near-infrared images and the laser scanning lattice;

(3) fusion detection of plant water stress: establish multi-variable linear regression with the water content and average values of texture and greyscale of the crop obtained on the basis of the near-infrared characteristic images of the crown layer acquired by the binocular multi-functional imaging system, the characteristic value of water stress index based on the plant crown-air temperature difference acquired with the infrared temperature sensor and the environmental temperature and humidity sensor, and the measured value of water content in the crop, i.e., establish a regression model with the chemically measured values of nitrogen, phosphorus and potassium as dependent variables and the average values of texture and greyscale and characteristic wavelengths as independent variables; that is to say, establish a regression model with the measured value of water content as an dependent variable and the water stress index and average values of texture and greyscale of the near-infrared images as independent variables; extract fused characteristic value of water content in the crop on the basis of the characteristics of the near-infrared images, infrared temperature sensor, and environmental temperature and humidity sensor;

(4) detection of plant pests and diseases: extract characteristic leaves affected by diseases on the basis of the visible light characteristic images of the crown layer and the near-infrared characteristic images of the crown layer acquired by the binocular multi-functional imaging system, and identify the types and severities of the crop diseases with a disease classification model; based on the visible light characteristic images of the crown layer and the near-infrared characteristic images of the crown layer acquired by the binocular multi-functional imaging system, compared the differences in time-series images to judge the severity of pest occurrence, and make a warning judgment on outbreak of pests and diseases with reference to the environmental temperature and humidity and historical weather information;

(5) synchronously acquire the environmental lighting and temperature and humidity information in the greenhouse with the environmental light intensity sensor and the environmental temperature and humidity sensors, correct the detected characteristic values of comprehensive plant growth information, to eliminate the interferences of environmental factors on the detection results;

(6) take the detected values of greenhouse crop and environment information which have been subjected to interference correction as result output values, and display them on a touch screen, and import the detection results into a database;

S5: after the plant information acquisition is completed, the PC sends an instruction to the DSP movement controller to drive the electronically-controlled head to rotate to the initial position and retract the lifting mechanism to the initial state according to preset route; the sliding platform travels to the next detection position according to a preset route; then the steps S3-S5 are repeated till the entire detection process is completed; then the sliding platform returns to the initial position.

2. The automatic monitoring method for greenhouse crop information based on a suspended slide rail platform according to claim 1, wherein, in the step 2.3), the movement of the sliding platform is set on a basis that the crown layer area detected at the initial detection position should account for more than 70% of the viewing field area and the distance from the plant top to the sensor is between 500 mm and 1,000 mm for single plant detection.

3. The automatic monitoring method for greenhouse crop information based on a suspended slide rail platform according to claim 1, wherein, in the step 4.2), the lattice data of height coordinate is filtered to remove redundant and invalid data under the following principle: for large-size crops, the height is valid if it is greater than 250 mm and smaller than 1,700 mm, and invalid data in the scanning process is removed on the basis of that threshold; for small-size crops and crops in the seedling stage, the height is valid if it is within a threshold interval of 20 mm-1,000 mm, and invalid data in the scanning process is removed on the basis of that threshold.

4. The automatic monitoring method for greenhouse crop information based on a suspended slide rail platform according to claim 1, wherein, the near-infrared characteristic images of the crown layer are near-infrared characteristic images at 930 nm and 1,420 nm.

5. The automatic monitoring method for greenhouse crop information based on a suspended slide rail platform according to claim 1, wherein, the PC is an industrial PC.

6. The automatic monitoring method for greenhouse crop information based on a suspended slide rail platform according to claim 1, wherein in step 3.1), the DSP movement controller sends a signal to a deceleration motor according to a position instruction sent from the PC, the deceleration motor drives a gear shaft to rotate with a gear, the gear is engaged with a rack and drives the entire sliding platform to move on the slide rail by pulleys.

* * * * *